United States Patent [19]

Steiner et al.

[11] Patent Number: 4,925,673
[45] Date of Patent: May 15, 1990

[54] DELIVERY SYSTEMS FOR PHARMACOLOGICAL AGENTS ENCAPSULATED WITH PROTEINOIDS

[75] Inventors: Solomon Steiner, Mt. Kisco; Robert Rosen, Rochester, both of N.Y.

[73] Assignee: Clinical Technologies Associates, Inc., Elmsford, N.Y.

[21] Appl. No.: 98,027

[22] PCT Filed: Aug. 14, 1987

[86] PCT No.: PCT/US87/02025

§ 371 Date: Sep. 8, 1987

§ 102(e) Date: Sep. 8, 1987

[87] PCT Pub. No.: WO88/01213

PCT Pub. Date: Feb. 25, 1988

Related U.S. Application Data

[63] Continuation-in-part of Ser. No. 897,361, Aug. 18, 1986, abandoned.

[51] Int. Cl.$^5$ .............................. A61K 9/66; A61J 5/04
[52] U.S. Cl. ........................................ 424/455; 264/4; 264/4.1; 424/451; 424/484
[58] Field of Search ............... 424/489, 490, 491, 455, 424/484; 264/4, 4.1

[56] References Cited

U.S. PATENT DOCUMENTS

| | | | |
|---|---|---|---|
| 3,962,416 | 6/1976 | Katzen | 424/479 X |
| 4,298,002 | 11/1981 | Ronel et al. | 424/424 |
| 4,352,883 | 10/1982 | Lim | 424/424 X |
| 4,613,500 | 9/1986 | Suzuki et al. | 424/494 X |
| 4,673,566 | 6/1987 | Goosen et al. | 424/458 X |

Primary Examiner—Thurman K. Page
Attorney, Agent, or Firm—Kilpatrick & Cody

[57] ABSTRACT

Methods are described for targeting the release of an active pharmacological agent in an animal by administering that agent encapsulated in proteinoid microspheres which are stable to the environment encountered from the point of introduction until they migrate to the targeted body organs, fluids or cells and are there unstable. Orally administered delivery systems for insulin, heparin and physostigmine utilize encapsulating microspheres which are predominantly of less than about 10 microns in diameter and pass readily through the gastrointestinal mucosa and which are made of an acidic proteinoid that is stable and unaffected by stomach enzymes and acid, but which releases the microencapsulated agent in pharmacologically active form in the near neutral blood stream. Basic proteinoid microspheres encapsulating a dopamine redox carrier system are administered in the weakly basic, where they are stable, and then enter the blood stream, where the encapsulated agent is similarly released.

23 Claims, No Drawings

DELIVERY SYSTEMS FOR PHARMACOLOGICAL AGENTS ENCAPSULATED WITH PROTEINOIDS

This is a continuation-in-part of copending application Ser. No. 897,361, which was filed Aug. 18, 1986 and now is abandoned.

BACKGROUND OF THE INVENTION

1. Field of the Invention

This invention relates to pharmacologically active agents which are encapsulated within protective proteinoid microspheres and the administration of same to warm blooded animals. It relates particularly to orally administered microspheres containing pharmacological agents which otherwise would be deactivated in the gastrointestinal tract.

2. Description of the Prior Art

The available modes of delivery of pharmceutical and therapeutic agents often are severely limited by chemical or physical barriers or both, which are imposed by the body. For example, oral delivery of many such agents would be the general method of choice if not for the numerous barriers faced by these agents along this route. Gastrointestinal conditions of inappropriate pH, the presence of powerful digestive enzymes, the permeability properties of gastrointestinal membranes and tissues and other factors all play important roles in determining the feasibility of oral delivery of active agents to their targets. Among the numerous pharmacological agents which are known to be adversely affected or rendered ineffective when administered orally are the biologically active polypeptides and proteins, such as insulin. These agents are rapidly destroyed in the stomach by acid hydrolysis and in the stomach and lower gastrointestinal tract by enzymes capable of cleaving peptide bonds and, in addition, they pass poorly, if at all, through the gastrointestinal wall.

A great deal of effort has been concentrated on the modification or isolation of the deleterious conditions within the gastrointestinal tract so that a pharmacological agent, which otherwise would be labile, could be absorbed through the stomach or intestine wall intact and in pharmacologically active form. The search in this area has been directed primarily in three directions; the co-administration of adjuvants, such as the resorcinols and the non-ionic surfactants polyoxyethylene oleyl ether and n-hexadecyl polyethylene ether; the co-administration of enzymatic inhibitors, such as pancreatic trypsin inhibitor, diisopropylfluorophosphate (DFP) and trasylol; and the use of liposomes, such as water-in-oil-in-water emulsions which provide a protective layer of lipid around the encorporated pharmacological agent and which represent the most successful approach to date. For example, the use of liposomes containing heparin is disclosed in U.S. Pat. No. 4,239,754 and several studies have been directed to the use of liposomes containing insulin; e.g., Patel et al, FEBS Letters, 62, 60 (1976) and Hashimoto et al, Endocrinol. Japan, 26, 337 (1979). In spite of these demonstrations of limited operability, the use of liposomes is still in the development stage and there are continuing problems, including poor stability and inadequate shelf life.

Accordingly, there remains a need for improved means for targeting the release of active pharmacological agents in the body and particularly for more satisfactory means for oral administration of pharmacological agents which are labile to conditions in the gastrointestinal tract.

SUMMARY OF THE INVENTION

It is an object of this invention to provide improved means for releasing a pharmacological agent in physiologically active form at a targeted body organ or fluid.

It is a further object of this invention to provide an improved delivery system for the enteric administration of pharmacological agents which, by themselves, pass slowly or not at all through the gastro-intestinal mucosa and/or are susceptible to chemical cleavage by acids and enzymes in the gastrointestinal tract.

It is a specific object to provide such delivery system in which the active pharmacological agent is encapsulated within a protective material which is itself pharmacologically harmless, which does not alter the physiological and biological properties of the active agent, which protects the active agent from the deleterious conditions within the gastrointestinal tract and which disappears or releases the active agent in the bloodstream or other target. It is a further specific object of this invention to provide such combination of active agent and protective material which is sufficiently lipophilic and of small particle size to pass rapidly through the gastrointestinal mucosa and which is simple to manufacture in bulk.

Additional objects of this invention are to provide methods of producing such delivery systems and of administering same to animals. It is a specific object to provide effective means for the oral delivery of insulin to diabetic mammals.

It has been found that these objects and other advantages, which will be apparent from this specification, are achieved by the invention described below.

Broadly, one aspect of this invention is a delivery system for an active pharmacological agent comprising said agent enclosed or encapsulated within proteinoid microspheres.

A second broad aspect of this invention is a method of encapsulating an active pharmacological agent comprising mixing said active agent with a pharmaceutically acceptable liquid and contacting said mixture with a proteinoid that interacts with said mixture to form hollow microspheres.

A third broad aspect of this invention is a method for targeting the release of a pharmacologically active agent in an animal comprising administering to said animal an effective amount of said active agent encapsulated within proteinoid microspheres, said micropheres being stable to the conditions encountered during migration from the point of introduction into said animal to a targeted release zone and being unstable at said zone.

DESCRIPTION OF THE PREFERRED EMBODIMENTS

Proteinoids, which form the protective capsules of this invention, have been described as artificial polypeptides, as they are man-made condensation polymers produced by random or directed assembly of natural or synthetic aminoacids and/or small peptide chains. Following the discovery, in the late 1950's, that linear condensation polymers of mixed natural aminoacids could interact with water to form hollow microspheres, proteinoids have been the subject of extensive investigations of the origin of life. An excellent review of these investigations, along with extensive bibliographies, is found in Fox, S. W. and Dose, K., *Molecular Evolution and the Origin of Life*, Marcel Dekker, Inc., New York (1977), the disclosure of which is incorporated herein by reference.

As a result of these and other studies, a great deal of knowledge has been accumulated concerning the preparation and properties of proteinoids and proteinoid microspheres. For example, it is known that proteinoids derived from the natural alpha-aminoacids (those found in animal or vegetable protein), as well as those incorporating other naturally occurring materials (such as) polynucleotides, phosphoric acid, iron and calcium), are non-toxic. It also has been found that inclusion in the polymer of a stoichiometric excess of acidic di or polycarboxylic aminoacid results in an acidic proteinoid which is insoluble in an acid environment and soluble in a basic environment, while inclusion of an excess of basic diamino or polyamino monomer results in a basic proteinoid that is soluble in an acidic medium aand insoluble at high pH. These solubility characteristics can be very finely tuned. Similarly, the size of the microspheres formed by contacting proteinoids with water or other liquid can be controlled within a range of from less that about one half micron to about ten microns or more by manipulating a variety of physical or chemical parameters, such as the pH, osmolarity or salt content of the liquid. It also has been observed that the proteinoids are far more resistant than proteins to cleavage by digestive enzymes.

The instant invention arose from the discovery that a pharmacologically active agent can be encapsulated within proteinoid microspheres simply by dissolving or suspending such agent in a pharmaceutically acceptable liquid, such as water or dimethyl sulfoxide, that interacts with that proteinoid to form microspheres.

It also has been discovered that such encapsulation does not alter the pharmacological properties of the active agent and that active agent bearing microspheres having diameters of less than about 10 microns are sufficiently small to pass readily through the gastrointestinal mucosa and enter the blood stream. The preferred range for rapid diffusion is from about 0.5 to about 5.0 microns, as smaller sizes exhibit somewhat less stability and incorporate relatively little active agent and larger sizes diffuse less readily. Particles of from about 5.0 to about 10 microns are, however, useful in admixture with those of the preferred range as their slower diffusion results in prolonged release of the active agent.

By tailoring both the solubility characteristics of an acidic proteinoid and the particle size of the microspheres by known means, it has been found to be possible to produce active agent bearing microspheres which are stable in the mouth (normal pH of from about 4 to about 6.8), which rapidly pass through the mucosa of the mouth into the bloodstream and which release the active agent in the blood (normal pH of from about 7.35 to about 7.45). Such systems are suitable for sublingual administration of pharmacological agents such as human or bovine growth hormone, interferon or interleukin-II.

Similarly, it is possible to produce readily diffusable microspheres from acidic proteinoids which are stable in the highly acidic stomach (normal pH of from about 2 to about 6), but which dissolve in the near neutral blood. Such systems are suitable for oral administration of peptide hormones, such as insulin, or heparin, which otherwise would be quickly destroyed in the stomach. They also are suitable for protecting the stomach from gastric irritants, such as aspirin. When such aspirin containing microspheres are orally administered, they pass through the gastrointestinal mucosa and release the aspirin in the bloodstream far more rapidly than conventional enterically coated aspirin, which first must traverse the stomach and then must enter the bloodstream from the intestine after the enteric coating has dissolved.

It also is possible to produce systems from basic proteinoids which are stable in the weakly basic lower digestive tract (normal pH of about 8), but which release active agent in the blood. Such systems are suitable for the administration of pharmacological agents such as calcium regulators and redox carrier systems for dopamine or gamma-aminobutyric acid.

In addition to these enterically administered delivery systems, it also is possible to produce a near neutral proteinoid microsphere system which is stable in the bloodstream, but which releases its content of pharmacological agent in response to the target organ environment, such as a higher or lower pH or the presence of a specific enzyme. Such near neutral systems must be introduced intravenously, unless the microspheres are sufficiently small to be encapsulated within larger proteinoid microspheres that are diffusable through the gastrointestinal mucosa and that are stable until they reach the bloodstream.

Although any pharmacological agent can be encapsulated within proteinoid microspheres, it obviously is of particular value for the protection of such agents which otherwise would be destroyed or rendered less effective by conditions encountered in the animal body before it reached its target zone.

Example 1, below, illustrates the preparation of an acidic thermal proteinoid that interacts with an aqueous solution of a pharmacologically active agent to encapsulate and protect that agent within hollow microspheres. These microspheres exhibit stability in the presence of the digestive enzymes and acid of the stomach and, being predominantly less than 5.0 microns in diameter, pass readily through the gastrointestinal mucosa into the weakly basic blood stream, where they dissolve and release the pharmacological agent.

EXAMPLE 1a

A stirred mixture of 52.3 g of aspartic acid (0.4 moles), 42 g of arginine hydrochloride (0.2 moles), 26 g of isoleucine (0.2 moles) and 50 ml of glycerol is heated under nitrogen to 160° C. with the evolution of gas. The temperature then is maintained at 155° C. for 23 hours, after which the mixture is cooled to room temperature, extracted with 200 ml of 10 wt % aqueous sodium bicarbonate and the extract dialized through a collodion membrane against distilled water for 26 hours, the water being changed every six hours. The content of the dialysis tubes then is evaporated to dryness at 50° C. under vacuum to yield a glassy solid acidic proteinoid material, which is ground to a fine powder.

EXAMPLE 1b

Thirty five mg of this powdered proteinoid is added to a mixture of 50 mg of porcine insulin crystals in 2 ml of distilled water and the mixture allowed to stand at room temperature until microspheres have formed. The insulin bearing microspheres are separated by filtration, washed with pH 5.4 aqueous acetic acid and then resuspended in 2 ml of pH 5.4 aqueous acetic acid. Microscopic examination of this suspension reveals stable microspheres that are predominantly between 0.1 and 5.0 microns in diameter. When a portion of the suspension is neutralized to pH 7.4 with concentrated ammonium hydroxide, dissolution of the microspheres is immediately evident.

EXAMPLE 1c

Each of three adult white rats having normal blood glucose levels is administered a dose of 0.35 ml of the insulin bearing microsphere suspension of Example 2b by a syringe inserted through the mouth and into the stomach. Following dosage, each of these animals exhibits a significant reduction in blood glucose, as measured in blood samples taken from the tail.

Although hollow microspheres suitable for encapsulating pharmacological agents can be formed from proteinoids derived from a single acidic or basic amino acid and as few as one other amino acid, a greater diversity of component amino acids often produces higher yields of uniform size microspheres within the desirable diameter range of 0.5 to 5.0 microns. Example 2 illustrates the effectiveness, in producing a hypoglycemic effect in mammals, of the oral administration of insulin encapsulated within a proteinoid derived from 18 different amino acids.

EXAMPLE 2a

A 250 ml filter flask containing 10 g of anhydrous dl-glutamic acid and 10 g of anhydrous dl-aspartic acid under nitrogen is heated in an oil bath at approximately 200° C. until the contents are molten. To this is added 5 g of an anhydrous equimolar mixture of the sixteen neutral and basic amino acids found in animal protein; i.e., alanine, arginine, asparagine, cysteine, glycine, histadine, leucine, lysine, methionine, phenylalanine, proline, serine, threonine, tyrosine, tryptophan and valine. The resulting mixture is stirred with a glass rod and maintained at 200° C. under nitrogen for three hours. After cooling, the amber product is extracted with a saturated aqueous solution of sodium bicarbonate and the resulting solution dialyzed through a collodion membrane against distilled water at room temperature for 24 hours, the water being changed every 6 hours. The content of the dialysis tubes then is acidified to pH 5.4 with concentrated acetic acid and centrifuged. After discarding the supernatant liquid, the insoluble solids are washed with pH 5.4 aqueous acetic acid and centrifuged again. This wash also is discarded and the solid proteinoid product is dried over silica gel overnight and then ground to a fine powder with mortar and pestle.

EXAMPLE 2b

A mixture of 50 mg of porcine insulin crystals in 2 ml of distilled water is added to 35 mg of the dry powdered proteinoid of Example 2a and the mixture allowed to stand at room temperature until microspheres have formed. The mixture is then centrifuged for 15 minutes. After discarding the supernatant liquid, the remaining microspheres are washed once with pH 5.4 aqueous acetic acid at room temperature and centrifuged for an additional 15 minutes. The supernatant liquid again is discarded and the insulin bearing proteinoid microspheres are resuspended in 2 ml of pH 5.4 aqueous acetic acid. Microscopic examination of the suspension shows that the microspheres are predominantly between 0.5 and 5.0 microns in diameter.

EXAMPLE 2c

Twelve male white rats, each weighing approximately 500 g and having a normal blood glucose level, are randomly assigned to four groups of three individuals for demonstrating the physiological efficacy of the oral administration of an aqueous suspension of insulin bearing proteinoid microspheres produced in accordance with the procedure of Example 2b, above. Between 0.35 and 0.5 ml of this aqueous suspension of microspheres is administered by gavage into the stomach of each rat in Group One. The Group Two rats have between 1.5 and 1.7 ml of the suspension similarly administered. The rats of Group Three receive 1.0 ml of distilled water similarly administered. The rats of Group Four similarly receive 25.0 mg of porcine insulin in 1.0 ml of distilled water. Both before and during the experiment, all animals are permitted free access to water and their normal feed. Blood glucose levels are measured on samples drawn from the tail at specific intervals after treatment and group averages are recorded in Table 1 as milligrams of glucose per deciliter of blood (mg/dl).

TABLE 1

| Ave. Blood Glucose (mg/dl) | | | | | | | |
|---|---|---|---|---|---|---|---|
| Group | Predose | 30 min. | 1 hr. | 1.5 hr. | 2 hr. | 2.5 hr. | 3 hr. |
| One | 135 | 85 | 88 | 66 | 44 | 27 | — |
| Two | — | — | — | — | — | 49 | — |
| Three | 120 | — | — | — | — | 119 | — |
| Four | 113 | 120 | 120 | 124 | 120 | — | 116 |
| Group | 4 hr. | 6 hr. | 12 hr. | 24 hr. | 36 hr. | 48 hr. | |
| One | 38 | — | 135 | 119 | 122 | — | |
| Two | 58 | — | 80 | 125 | 125 | 122 | |
| Three | 122 | — | — | 119 | 124 | — | |
| Four | 111 | 123 | — | — | — | — | |

It is clear from the data in Table 1 that insulin is delivered in a physiologically meaningful and active fashion via the oral route with acidic proteinoid microspheres. In all animals receiving insulin containing microspheres, the blood glucose level returns to the preadministration level without any observed adverse effect. It should be noted that the administration of larger doses of insulin containing microspheres to the Group Two animals appears to increase the duration of action rather than the magnitude of the effect. It also should be noted that the oral administration of far larger dosages per unit of body weight of unprotected porcine or bovine insulin to laboratory animals and humans produces no detectable reduction of blood glucose levels.

Similarly effective insulin bearing proteinoid microspheres can be produced by contacting a dry powered acidic proteinoid, such as those of Examples 1a or 2a, with insulin suspended or dissolved in a wide variety of pharmaceutically acceptable liquids, including aqueous solutions of ethanol, isopropanol, terpenol, dimethyl sulfoxide, starch, Tweens 80 and cyclodextran.

Example 3 illustrates an especially preferred method of producing insulin bearing proteinoid microspheres which reliably produces high yields of microspheres that fall within the desirable diameter range of 0.5 to 5.0 microns and that are readily soluble at the pH of the targeted blood.

EXAMPLE 3a

A flask containing 2 parts by weight of anhydrous l-glutamic acid under a stream of nitrogen is heated in an oil bath at approximately 175° C. until the contents are molten. To this is added 2 parts by weight of anhydrous l-aspartic acid and one part by weight of an anhydrous equimolar mixture of the sixteen neutral and basic amino acids found in animal protein. The resulting mixture is stirred with a glass rod and maintained at 175° C. under nitrogen for three hours. After cooling, the dark amber product is extracted with saturated aqueous sodium bicarbonate and the extract dialyzed through a collodion membrane against distilled water at room temperature for 24 hours, the water being changed every four hours. The entire content of the dialysis tubes then is dried under vacuum at 65° and the residual solids are ground to a fine powder with mortar and pestle.

EXAMPLE 3b

An aqueous solution of proteinoid is produced by mixing 35 mg of the powder of Example 3a per ml of water, adjusting the pH to 7.4 with concentrated aqueous sodium bicarbonate and removing any insoluble materials by filtration. One part by volume of this solids free solution of proteinoid then is rapidly injected into an equal volume of a freshly prepared 25 mg/ml solution of porcine insulin in pH 2.25 aqueous acetic acid. The mixture, which has a pH of approximately 3.5, is stirred in an ice bath for 15 minutes and filtered to separate the insulin bearing microspheres from the filtrate which is discarded. After washing twice with pH 3.5 aqueous acetic acid, the microspheres are resuspended in 10 parts by volume of pH 3.5 aqueous acetic acid. Microscopic examination of a portion of this suspension shows a high yield of microspheres which are predominantly between 0.5 and 5.0 microns in diameter and which dissolve rapidly when the suspension is neutralized to pH 7.4 by the addition of concentrated aqueous sodium bicarbonate.

In the following Example 4, dosages of the insulin bearing microsphere suspension of Example 3b are referred to as "insulin filled microspheres". Microspheres which contain no encapsulated insulin are produced by repeating the procedure of Example 3b, except that the insulin is omitted during the formation of microspheres and the microspheres are suspended in a 2.5 mg/ml solution of porcine insulin in distilled water, rather than in dilute acetic acid. Doses of the resulting suspension, which contain no insulin within the microspheres, are referred to as "microspheres with external insulin". Dosages of the 2.5 mg/ml solution of porcine insulin alone are referred to as "raw insulin".

EXAMPLE 4

Twelve male white rats, each weighing approximately 500 g and havinng a normal blood glucose level, are arbitrarily assigned to two groups of three animals and a third group of six animals. The three animals of group A are administered the insulin filled microspheres by gavage and the three animals of group B are similarly administered the microspheres with external insulin. The six animals of group C similarly receive the raw insulin. All dosages are 1 ml/500 g of body weight and all animals are tested for blood glucose immediately before dosage and at intervals thereafter. The average blood glucose level for the animals in each group is shown in Table 2.

TABLE 2

| | Blood Glucose (mg/dl) in Rats | | |
|---|---|---|---|
| | Group (Treatment) | | |
| Time (hrs) | A (Insulin Filled Microspheres) | B (Microspheres with External Insulin) | C (Raw Insulin) |
| 0 | 109.7 | 92 | 92.7 |
| .5 | 54.7 | 89.3 | 95.5 |
| 1 | 59 | 84.3 | 98.2 |
| 2 | 50 | 80.7 | 95.8 |
| 3 | 57.7 | 86.7 | 86.2 |
| 4 | 64.7 | 84 | 91 |
| 6 | 76 | 83.7 | 89.8 |
| 8 | 65.7 | 88.7 | 91 |
| 12 | 81.7 | 92.3 | 92 |
| 24 | 94.3 | 95.7 | 92 |

These experiments show no significant effect on blood glucose levels of either the raw insulin or the microspheres with external insulin. In contrast, the insulin filled microspheres produce a peak reduction of approximately 50% and an effect of long duration. This demonstrates that the acidic proteinoid microspheres have no effect on blood glucose levels and that they protect only the encapsulated insulin from the hostile environment of the stomach, thereby enabling that encapsulated insulin to enter the blood stream in physiologically active form.

EXAMPLE 5a

Diabetes mellitis is induced in rats weighing approximately 300 g by giving each a 75 mg/kg body weight intravenous injection of streptozotocin. Ten rats which are observed to show consistently high blood glucose levels, polyuria and polydipsia and must be maintained on subcutaneous injections of porcine insulin are selected for this experiment.

EXAMPLE 5b

Three of the diabetic rats are administered by gavage approximately 1 ml of the aqueous suspension of porcine insulin bearing acidic proteinoid microspheres of Example 3b. A fourth diabetic rat has 3 ml of the suspension in 50 ml of tap water placed in its water bottle and this rat self administers his dose. All of the rats are food deprived for 12 hours prior to dosing. In all subjects, the oral administration of the microencapsulated insulin produces a significant and prolonged reduction in blood glucose levels.

EXAMPLE 5c

The remaining six diabetic rats are arbitrarily assigned to three groups of two animals. The animals of the first group are administered by gavage 1 ml of the aqueous suspension of porcine insulin bearing acidic proteinoid microspheres of Example 3b. The animals of the second and third groups receive subcutaneous injections of 0.25 mg (6.5 I.U.) and 0.125 mg (3.25 I.U.), respectively, of porcine insulin. Blood glucose measurements are made on all animals immediately before dosing and at intervals thereafter. The animal groups are crossed over twice at one week intervals, so that all of the animals receive each of the insulin treatments. The average percent decrease from baseline blood glucose levels for each treatment is shown in Table 3.

TABLE 3

| Insulin Treatment | % Decrease from Baseline Blood Glucose in Rats Time (hrs.) after Dosage | | | | | | | | | | |
|---|---|---|---|---|---|---|---|---|---|---|---|
| | 0.5 | 1 | 1.5 | 2 | 3 | 4 | 6 | 8 | 12 | 24 | 48 |
| Microspheres Oral | 29 | 38 | 45 | 44 | 48 | 50 | 51 | 40 | 37 | 24 | −27 |
| 0.25 mg SC | 28 | 55 | 72 | 77 | 84 | 79 | 34 | 4 | 3 | −7 | −5 |
| 0.125 mg SC | 5 | 17 | 27 | 45 | 47 | 29 | 8 | −8 | −8 | −8 | −8 |

These results demonstrate that the peak effect of the orally administered dose of insulin filled microspheres on diabetic rats is comparable to a subcutaneous injection of 0.125 mg of insulin and that the duration of the effect is significantly longer than that produced by either a 0.125 mg or a 0.25 mg subcutaneous injection.

EXAMPLE 6

One ml of the aqueous suspension of porcine insulin bearing acidic proteinoid microspheres of Example 3b is administered by gavage into the stomach of each of three adult guinea pigs weighing approximately 800 g. Blood samples are taken immediately before and at intervals after administration of the dosage.

The blood samples from guinea pig #1 are tested for blood glucose, which drops from a predosage level of 160 mg/dl to 42 mg/dl in one half hour and to 25 mg/dl in 1.5 hours, where it remains for an additional 1.5 hours, at which time symptoms of insulin shock are observed and the animal is revived by orally administered glucose.

The blood samples from guinea pigs #2 and #3 are tested for porcine insulin with radioimmuno assay kits, which are marketed by Cambridge Medical Diagnostics. This method, which distinguishes between porcine and guinea pig insulin, shows that the predosage level of porcine insulin in the blood of both guinea pigs #2 and #3 is zero. In guinea pig #2 the concentration peaks at 250 micrograms/ml one and one half hours after oral administration of the microspheres and in guinea pig #3 a peak of 240 micrograms/ml is reached in four hours.

These experiments demonstrate that the orally administered porcine insulin has a powerful hypoglycemic effect in a guinea pig, that it actually enters the blood stream and that its administration does not merely stimulate guinea pig insulin production by the animal.

EXAMPLE 7a

The procedure of Example 3b is repeated, except that the insulin filled microspheres are suspended in aqueous acetic acid having a pH of 2.25, rather than 3.5. A sealed vial of this suspension is stored at room temperature for 23 days.

EXAMPLE 7b

The activity of the thus aged encapsulated insulin is tested by administering the suspension by gavage to the stomachs of adult rats which have been deprived of food for eight hours and then measuring blood glucose levels at intervals after dosage. The results are shown in Table 4.

TABLE 4

| Rat # | weight (g) | dose (ml) | Blood Glucose (mg/dl) Time after Dosage (hrs.) | | | | | |
|---|---|---|---|---|---|---|---|---|
| | | | 0 | 0.5 | 1.0 | 1.5 | 2.0 | 3.0 |
| 40 | 398 | 0.40 | 64 | 49 | 44 | 34 | 33 | 35 |
| 41 | 415 | 0.42 | 79 | 89 | 35 | 82 | 80 | 80 |
| 42 | 479 | 0.48 | 79 | 50 | 34 | 37 | 37 | 49 |

Normally insulin in solution can be expected to degrade within a few days, even when refrigerated. The magnitude of the blood sugar reduction in all of thes rats and the prolonged effect shown by rats #40 and 42 indicate that insulin solution stability is improved by encapsulation within acidic proteinoid microspheres.

EXAMPLE 7c

The aged suspension of encapsulated insulin is added to human serum and, employing a standard laboratory haemocytometer counting technique, the number of microspheres are counted immediately after mixing and at intervals thereafter. Table 5 shows the number of microspheres observable as a function of time.

TABLE 5

| Dissolution of Microspheres in Human Serum | | | | |
|---|---|---|---|---|
| Time (minutes) | 0 | 3 | 30 | 60 |
| Microspheres (× 1000) | 78 | 50 | 19 | 9 |

This data demonstrates that insulin bearing acidic proteinoid microspheres which have remained intact after 23 days exposure at room temperature to pH 2.25 aqueous acetic acid still dissolve rapidly in near neutral human serum.

EXAMPLE 8a

An aqueous solution of heparin containing 250 mg/ml of heparin is adjusted to pH 4.5 by the addition of concentrated acetic acid. To this is added 35 mg/ml of the dry powdered acidic proteinoid of Example 3a and the mixture is allowed to stand at room temperature until microspheres have formed. One part by volume of the mixture then is centrifuged and, after discarding the supernatant liquid, the heparin bearing microspheres are washed with pH 4.5 aqueous acetic acid, filtered and resuspended in pH 4.5 aqueous acetic acid, the suspension being made up to one part by volume. Microscopic examination reveals that the microspheres are predominantly within the range of from about 0.1 to about 5 microns in diameter, with the majority being between 1 and 2 microns.

EXAMPLE 8b

Seven male white rats, each weighing approximately 600 g, are deprived of food for 12 hours before the start of the experiment. Rat #1 receives no treatment. Rat #2 receives an intravenous injection of 250 mg of heparin in one ml of distilled water. Each of rats #3-7 has 1 ml of the aqueous suspension of heparin bearing microspheres of Example 8a introduced directly into the stomach by gavage. The effect of heparin is determined using the Activated Partial Thromboplastin Time (APTT) test. This test measures the time necessary for a sample of serum taken from the tail vein to form a fibrin clot. The results for each rat at various times after dosing are shown in Table 6.

TABLE 6

| | | Time to Coagulation in the APTT Test (seconds) | | | | | |
|---|---|---|---|---|---|---|---|
| Rat # | Heparin Treatment | Pre-dose | 1 hr. | 2 hrs. | 3 hrs. | 4 hrs. | 24 hrs. |
| 1 | none | 28 | 26 | 27 | — | — | — |
| 2 | IV | 25 | 54 | >300 | — | — | — |
| 3 | microspheres | 24 | 35 | >300 | — | — | — |
| 4 | " | 26 | 35 | 59 | 118 | >300 | 21 |
| 5 | " | 29 | 41 | 63 | 106 | 248 | 26 |
| 6 | " | 25 | 37 | 66 | 121 | >300 | 23 |
| 7 | " | 24 | 31 | 62 | 111 | >300 | 37 |

In all animals receiving heparin bearing microspheres, coagulation time increases to a level comparable to that seen following an intravenous injection of heparin. It is clear from this data that heparin is delivered to the bloodstream in a physiologically meaningful and active fashion when encapsulated in acidic proteinoid microspheres and administered orally. It should be noted that the oral administration of far larger doses per unit of body weight of unprotected heparin to laboratory animals and humans produces no detectable increase in coagulation time.

EXAMPLE 9a

An aqueous solution of physostigmine containing 50 mg/ml of physostigmine is adjusted to pH 5 by the addition of concentrated acetic acid. To one volume of this solution is added 100 mg per ml of the dry powdered acidic proteinoid of Example 3a and the mixture is allowed to stand at room temperature until microspheres have formed. It then is filtered, washed three times with pH 5 aqueous acetic acid and the separated microspheres are resuspended in one volume of pH 5 acetic acid. Microscopic examination reveals that the suspended microspheres are predominantly 0.5–5.0 microns in diameter.

EXAMPLE 9b

Each of two normal rats weighing about 360 g is administered by gavage 3 ml of the suspension of physostigmine bearing microspheres. Within 30 minutes of dosage, both animals have died and each exhibits enlarged liver and peritoneal hemorrhage. These lethal oral dosages of microencapsulated physostigmine are calculated to be less than one percent of the $LD_{50}$ oral dosage of unprotected physostigmine in rats.

In addition to the specific pharmacological agents that are shown by the above examples to be released in the blood stream in physiologically active form when orally administered within protective acidic proteinoid microspheres, such microsphere delivery system is similarly effective with a wide variety of other agents which are labile in the stomach invironment, including nitroglycerin, Salk polio vaccine, rubella vaccine and hepatitis B vaccine. There are, however many other pharmacological agents which could be deleteriously affected by even the mildly acidic conditions encountered during encapsulation within acidic proteinoid microspheres.

The following experiment demonstrates the ability of a basic proteinoid to form microspheres which encapsulate and protect one such extremely acid sensitive pharmacological agent, a dopamine derivative, from the hostile environment of the gastrointestinal tract, as well as to deliver that agent to the circulatory system, from which it penetrates the brain blood barrier and releases dopamine in the brain. The dopamine derivative employed in this experiment is PR-21, which is a proprietary composition of acylated dopamine bonded to a reduced dihydropyridine/pyridinium salt type redox carrier which was developed by Pharmatek, Inc. and is described in U.S. Pat. No. 4,479,932. The unprotected PR-21 composition is unstable anywhere in the gastrointestinal tract and is particularly sensitive to acid conditions. When injected intravenously into rats, significant amounts of the deacylated quaternary precursor of dopamine can be measured in the homogenized rat brain by the method of Bodir and Farog, Journal of Medicinal Chemistry, 26, 528 (1983).

EXAMPLE 10a

A nitrogen swept mixture of two parts by weight of arginine, two parts by weight of lysine and one part by weight of an equimolar mixture of the sixteen neutral and acidic aminoacids found in animal protein is stirred and heated at 180° C. for 3 hours. The cooled reaction mixture is extracted with pH 2.25 aqueous acetic acid and the extract is dialyzed through a collodion membrane against a large volume of distilled water at room temperature for 48 hours, the water being changed every six hours. The content of the dialysis tubes then is heated under vacuum at 65° C. to yield a dry powdered basic proteinoid. When suspended in a moderate to strongly alkaline liquid environment, this powdered proteinoid spontaneously forms hollow microspheres which are stable in that environment, but which dissolve at the near neutral pH of blood.

EXAMPLE 10b

One part by volume of an ethanol solution of PR-21 (360 mg/ml) is diluted with an equal volume of distilled water and the pH of the solution is adjusted to 8 by the addition of saturated aqueous monobasic potassium phosphate buffer. A portion of this buffered solution, which contains 180 mg/ml of PR-21, is set aside and dosages of it are referred to below as "unprotected PR-21".

The remainder of the buffered solution is mixed with 25 mg/ml of the dry powdered basic proteinoid of Example 10a and chilled in an ice bath until microspheres have formed. Dosages of the resulting suspension, in which the microspheres are predominantly 0.1 to 5 microns in diameter, are referred to below as "microencapsulated PR-21".

EXAMPLE 10c

Two rats weighing about 500 g (rats DA-1 and DA-2) are anesthetized, the jejunum is externalized and the sphincter is tied off to prevent backwash into the stomach. Two ml of microencapsulated PR-21 are then injected into the jejunum of each rat. Two similar control rats (rats DA-5 and DA-6) are similarly prepared, but are injected in the jejunum with 2 ml of unprotected PR-21. Finally, two similar control rats (rats DA-3 and DA-4) are intravenously injected with 2 ml of unprotected PR-21. Table 7 shows the amount of deacylated quaternary precursor of dopamine that is detectable in the homogenized brains of the six subjects.

TABLE 7

| | Dopamine Quaternary Precursor in Rat Brains | |
|---|---|---|
| Rat # | Treatment | Precursor (micrograms/g) |
| DA-1 | Intestinal Injection, Microencapsulated PR-21 | 1 |
| DA-2 | Intestinal Injection, Microencapsulated PR-21 | 10 |
| DA-3 | IV Injection, Unprotected PR-21 | 3 |
| DA-4 | IV Injection, Unprotected PR-21 | 4.5 |
| DA-5 | Intestinal Injection, Unprotected PR-21 | 0 |
| DA-6 | Intestinal Injection, Unprotected PR-21 | 0 |

These results demonstrate the capacity of basic proteinoid microspheres to encapsulate and protect a dopamine derivative from the digestive enzymes and basic environment of the intestine, as well as the fact that such microspheres are transported across the gastrointestinal mucosa into the rear neutral blood stream where the encapsulated dopamine derivative is released. For successful oral delivery of such encapsulated pharmacological agent, the acid sensitive basic proteinoid microspheres must be protected while traversing the mouth and stomach. Advantageously, this is accomplished by a conventional enteric coating which does not dissolve until it reaches the intestine.

EXAMPLE 11

A stirred mixture of 2 mole parts of anhydrous glutamic acid, 2 mole parts of lysine and 1 mole part of an equimolar mixture of neutral aminoacids (alanine, glycine, leucine, phenylalanine, proline, tyrosine and valine) is heated under nitrogen at 170° C. for four hours. The cooled reaction product is extracted with pH 2.25 aqueous acetic acid and the extract dialyzed through a collodion membrane against distilled water for 24 hours, the water being changed every 4 hours. The content of the dialysis tubes is evaporated to dryness at 65° C. under vacuum and the residual solids are ground to a fine powder. When added to a pH 7.4 aqueous solution or suspension of a pharmacological agent, this neutral powdered proteinoid spontaneously forms a profusion of hollow microspheres which encapsulate that solution or suspension.

These microspheres are stable in human serum, but dissolve rapidly in pH 2.5 aqueous acid to release their contents. Being destabitized by exposure to reduced pH, such as that encountered when engulfed within macrophages, these neutral proteinoid microspheres are suited for the intravenous adminstration of a pharmacological agent, such as azidothymidine, which, in unprotected form, is quickly absorbed by many untargeted body tissues and cells, as well as the targeted macrophages.

It will be apparent to those of ordinary skill in the art that numerous changes and modifications can be made in the illustrative embodiments of the invention described above without departing from the spirit or scope of the invention as set forth in the following claims.

We claim:

1. Composition comprising a pharmacologically active agent encapsulated within protenoid microspheres having diameters predominantly less than about 10 microns and formed from linear thermal condensation polymers of mixed amino acids.

2. Composition of claim 1 wherein said microspheres are stable in at least a segment of the gastrointestinal tract, are unstable in the blood stream and are predominatly less than about 10 microns in diameter so as to readily penetrate the gastrointestinal mucosa and release said active agent in the blood stream in physiologically active form.

3. Composition of claim 2 wherein said polymer is acidic and said microspheres are stable to acids and enzymes in the mouth.

4. Composition of claim 2 wherein said polymer is basic and said microspheres are stable in the weakly basic lower digestive tract.

5. Composition of claim 4 wherein said pharmacological agent is a dopamine redox carrier system.

6. Composition of claim 2 wherein said polymer is acidic and said microspheres are stable to acids and enzymes in the stomach.

7. Composition of claim 6 wherein said pharmacological agent is insulin.

8. Composition of claim 6 wherein said pharmacological agent is heparin.

9. Composition of claim 6 wherein said pharmacological agent is physostigmine.

10. Composition of claim 1 wherein said polymer is neutral and said microspheres are stable in the blood stream and are unstable at reduced pH.

11. Composition of claim 1 wherein said microspheres are predominantly from about 0.5 to about 5.0 microns in diameter.

12. Method for microencapsulating a pharmacologically active agent within microspheres for targeted release within a selected pH range comprising forming a mixture of said agent with a pharmaceutically acceptable liquid, said mixture having a pH outside said selected range, and contacting said mixture with proteinoids formed of linear thermal condensation polymers of mixed amino acids which are soluble within said selected pH range and insoluble in said mixture to form microspheres having diameters predominately less than about 10 microns containing the active agent.

13. Method of claim 12 wherein said pharmaceutically acceptable liquid is water.

14. Method of claim 12 including preliminary purification of said polymers by mixing the polymers with water having a pH within said selected range and separating the resulting aqueous solution of said polymers from any insoluble material.

15. Method for producing an orally administerable composition for delivering insulin to the blood stream in physiologically active form comprising mixing insulin with water and contacting said mixture with a thermal condensation polymer derived from about two parts glutamic acid, about two parts aspartic acid and about one part of neutral or basic alpha-aminoacid.

16. Method for targeting release of a pharmacologically active agent in an animal comprising administering to said animal an effective amount of said active agent encapsulated within proteinoid microspheres formed from linear thermal condensation polymers of mixed amino acids having diameters predominately less than about 10 microns, said microspheres being stable to the conditions encountered during migration from the point of introduction into said animal to a targeted release zone and being unstable at said zone.

17. Method of claim 16 wherein said microspheres are predominantly from about 0.5 to about 5.0 microns in diameter.

18. Method of claim 16 wherein said microspheres are enterically administered for targeted release in the blood stream and said microspheres are stable in that segment of the gastrointestinal tract into which they are introduced and are unstable in the blood stream.

19. Method of claim 18 wherein said encapsulated active agent is sublingually introduced into the bloodstream and said microspheres are sufficiently acidic to be stable at a pH of from about 4 to about 6.8 and unstable at a pH of from about 7.35 to about 7.45.

20. Method of claim 18 wherein said encapsulated active agent is introduced into the bloodstream from the weakly basic lower gastrointestinal tract and said microspheres are sufficiently basic to be stable at a pH of about 8 and unstable at a pH of from about 7.35 to about 7.45.

21. Method of claim 18 wherein said encapsulated active agent is gastrically introduced into the bloodstream and said microspheres are sufficiently acidic to be stable at a pH of from about 2 to about 6 and unstable at a pH of from about 7.35 to about 7.45.

22. Method of claim 16 wherein said microspheres are intravenously administered and are stable at a pH of from about 7.35 to about 7.45 and unstable at reduced pH.

23. Method of treating a diabetic conditions in an animal comprising orally administering to said animal an effective amount of insulin which is encapsulated within acidic protenoid microspheres formed from linear thermal condensation polymers of mixed amino acids, said microspheres being predominantly from about 0.5 to about 5.0 microns in diameter, stable at a pH of up to about 6 and unstable at a pH of from about 7.35 to about 7.45.

* * * * *